(12) United States Patent
Van Oort et al.

(10) Patent No.: US 6,695,790 B2
(45) Date of Patent: Feb. 24, 2004

(54) METHOD AND SYSTEM FOR DETERMINING KIDNEY FAILURE

(75) Inventors: Geeske Van Oort, Rosmalen (NL); Jos W. J. Van Hove, Schiedam (NL)

(73) Assignee: Medtronic, Inc., Minneapolis, MN (US)

( * ) Notice: Subject to any disclaimer, the term of this patent is extended or adjusted under 35 U.S.C. 154(b) by 300 days.

(21) Appl. No.: 09/984,087

(22) Filed: Oct. 26, 2001

(65) Prior Publication Data

US 2003/0083585 A1 May 1, 2003

(51) Int. Cl.[7] ................................................. A61B 5/04
(52) U.S. Cl. ........................... 600/508; 600/509; 607/9
(58) Field of Search ................... 607/2, 3, 9; 600/508, 600/509

(56) References Cited

U.S. PATENT DOCUMENTS

| | | | |
|---|---|---|---|
| 4,316,472 A | 2/1982 | Mirowski et al. | 607/9 |
| 4,384,585 A | 5/1983 | Zipes | 607/5 |
| 4,476,868 A | 10/1984 | Thompson et al. | 607/14 |
| 4,556,063 A | 12/1985 | Thompson et al. | 712/241 |
| 4,577,633 A | 3/1986 | Berkovits et al. | 607/15 |
| 4,587,970 A | 5/1986 | Holley et al. | 607/15 |
| 4,716,887 A | 1/1988 | Koning et al. | 607/24 |
| 4,726,380 A | 2/1988 | Vollmann | 607/15 |
| 4,727,877 A | 3/1988 | Kallok | 607/5 |
| 4,750,494 A | 6/1988 | King | 607/14 |
| 4,800,883 A | 1/1989 | Winstrom | 116/10 |
| 4,821,723 A | 4/1989 | Baker et al. | 607/7 |
| 4,830,006 A | 5/1989 | Haluska et al. | 607/4 |
| 4,880,005 A | 11/1989 | Pless | 607/15 |
| 4,899,750 A | 2/1990 | Ekwall | 607/28 |
| 4,949,719 A | 8/1990 | Pless | 607/7 |
| 4,953,551 A | 9/1990 | Mehra | 607/5 |
| 5,117,824 A | 6/1992 | Keimel | 607/4 |
| 5,144,949 A | 9/1992 | Olson | 607/17 |
| 5,158,078 A | 10/1992 | Bennett | 607/27 |
| 5,163,427 A | 11/1992 | Keimel | 607/5 |
| 5,188,105 A | 2/1993 | Keimel | 607/5 |
| 5,199,428 A | 4/1993 | Obel et al. | 607/44 |
| 5,207,218 A | 5/1993 | Carpentier | 607/36 |
| 5,269,298 A | 12/1993 | Adams et al. | 607/5 |
| 5,312,453 A | 5/1994 | Shelton et al. | 607/19 |
| 5,314,430 A | 5/1994 | Bordy | 607/5 |
| 5,330,507 A | 7/1994 | Schwartz | 607/14 |
| 5,331,966 A | 7/1994 | Bennett | 600/508 |
| 5,354,316 A | 10/1994 | Keimel | 607/15 |
| 6,029,087 A | 2/2000 | Wohlgemuth | 607/9 |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

"Automatic Tachycardia Recognition" Arzbaecher et al. PACE, May–Jun. 1984 p. 541–547.

*Primary Examiner*—Carl Layno
(74) *Attorney, Agent, or Firm*—Girma Wolde-Michael

(57) ABSTRACT

A method of determining kidney failure in a patient using an implantable medical device is described. In one embodiment, a first magnitude of a first polarization signal is measured. An additional magnitude of an additional polarization signal is measured after a first interval. A deflection differential between the first magnitude and the additional magnitude is determined and kidney failure in the patient is determined when the deflection differential is greater than an established threshold.

62 Claims, 8 Drawing Sheets

METHOD AND SYSTEM FOR DETERMINING KIDNEY FAILURE

FIELD OF THE INVENTION

The present invention relates to the field of implantable medical devices. More particularly, the present invention relates to cardiac pacing systems that are capable of measure and compare polarization signals to thereby determine an occurrence of a kidney failure.

BACKGROUND OF THE INVENTION

Implantable pulse generators (or IPGS) are well known in the prior art. After a stimulus in the heart, a charge builds up at the electrode tip, which results in a polarization signal that decays over time. While an initial magnitude of the polarization signal is dependent upon the configuration of the electrode as well as any fibrosis around the electrode tip, ionic concentration in the blood ambient the heart is a major factor in the generation of the initial magnitude. For a patient having a significant risk of experiencing kidney failure, the ionic concentration may increase with each succeeding dialysis of the patient. However, the medical arts have failed to utilize various measurements of the polarization signal to ascertain any increases in the ionic concentration with each succeeding dialysis of the patient.

Thus, prior to the present invention, a need existed in the medical arts for facilitating a determination of a kidney failure by a patient.

Several methods have been proposed in the prior art for to determine various concentrations within the heart of a patient.

For example, U.S. Pat. No. 4,716,887 to Koning et al., entitled "Apparatus And Method For Adjusting Heart/Pacer Rate Relative To Cardiac $PCO_2$ To Obtain A Required Cardiac Output," hereby incorporated by reference in its entirety, discloses pacing pulses to the right ventricle of the heart and a $pCO_2$ sensor for sensing $pCO_2$ of the blood in the heart. A microprocessor is programmed to relate the $pCO_2$ with the required heart rate or change in rate, •R, needed to supply a desired cardiac output and to cause the pacer to pace the heart at the required heart rate when the heart is not naturally paced.

U.S. Pat. No. 4,705,494 to King, entitled "Automatic Implantable Fibrillation Preventer," hereby incorporated by reference in its entirety, discloses a dual sensing of the probable onset of ventricular fibrillation or other harmful tachyarrythmias and delivering electrical cardioverting stimulation pulses in response thereto. One sensing technique utilizes an intracardiac ECG observed within three dimensional space. The other sensing technique employs a chemically sensitive semiconductor device which measures the level of ionic potassium found within the intracardiac blood.

U.S. Pat. No. 4,899,750 to Ekwall. entitled "Lead Impedance Scanning System For Pacemakers", hereby incorporated by reference in its entirety, discloses making separate measurements of lead impedance during each heart signal and each pacing pulse. A moving average of measures parameters is maintained and recurring deviations from the norms are noted in separate event counters for subsequent analysis of the noted events as possible indications of impending failure of an implanted lead.

As discussed above, the most pertinent prior art patents are shown in the following table:

TABLE 1

Prior Art Patents.

| U.S. Pat. No. | Date | Inventor(s) |
| --- | --- | --- |
| US 4,716,887 | Jan. 5, 1988 | Koning et al. |
| US 4,750,494 | Jun. 14, 1988 | King |
| US 4,899,750 | Feb. 13, 1990 | Ekwall |

All the patents listed in Table 1 are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a method and system for managing therapies in a cardiac pacing system. Such a system of the present invention overcomes the problems, disadvantages and limitations of the prior art described above, and provides a more efficient and accurate means of determining kidney failure in a patient.

The present invention has certain objects. That is, various embodiments of the present invention provide solutions to one or more problems existing in the prior art respecting the determination of kidney failure in a patient. Those problems include, without limitation: the lack of knowledge relating to an interpretation of any deflections in a polarization signal as an indication of kidney failure; inability to use ambient heart conditions as indication of kidney failure; inability to track likelihood of kidney failure with succeeding dialysis sessions; inability to determine risk of kidney failure using measurements of the polarization signal; and inability to correlate polarization signal magnitude with potential kidney failure.

In comparison to known techniques for determining kidney failure, various embodiments of the present invention may provide the following advantages, interalia, i.e., use of an implantable medical device in determining an occurrence of kidney failure in a patient; ability to determine ionic concentration in the blood ambient the heart; ability to correlate ionic concentration in the blood with magnitude of a polarization signal; ability to measure potential risk of kidney failure with each succeeding dialysis based on ionic concentration; ability to correlate risk of kidney failure with polarization signals measured by an implantable medical device; and use of one implantable medical device to provide pacing stimulation and concomitantly, to measure potential kidney failure.

Some embodiments of the present invention include one or more of the following features: (a) an IPG capable of measuring ionic concentration in the blood; (b) an IPG capable of determining magnitudes of polarization signals; (c) an IPG capable of correlating ionic concentration with magnitudes of polarization signals; (d) an IPG capable of determining potential kidney failure based on ambient heart conditions; (e) an IPG capable of correlating polarization signals with risk of kidney failure over a period of time (f) methods of determining potential kidney failure based on ambient heart conditions; and (g) methods of correlating magnitudes of polarization signals with risk of kidney failure over time.

At least some embodiments of the invention provide methods for determining kidney failure, such as: (a) a first magnitude of a first polarization signal being determined during a first visit of the patient for a dialysis treatment, a second magnitude of a second polarization signal being determined during a second visit of the patient for a dialysis treatment, and a deflection differential between the first magnitude and the second magnitude being determined and the probability or existence of kidney failure being determined for the patient when the deflection differential exceeds or is greater than an established threshold; (b) a series of discrete and individual historical or chronological polarization signal trends being calculated by comparing a series of presently measured polarization signals respecting previously measured polarization signals, where the polarization trend signals are calculated and stored in memory at predetermined intervals for subsequent retrieval or signal processing; (c) discrete or individual polarization trend signals being employed to alert or warn the patient or a health care professional that the patient has a probability of or is experiencing kidney failure in response to a predetermined polarization trend signal threshold being reached or exceeded; (d) a warning or alert being provided to a remote health care provider through internet or telephonic communication between the implantable medical device and a remote computer, server or database; (e) in response to a warning or alert being generated, the patient and/or health care provider being prompted to arrange dialysis treatment for the patient within a specified time period.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE
PREFERRED EMBODIMENTS OF THE
INVENTION

Figure 1:
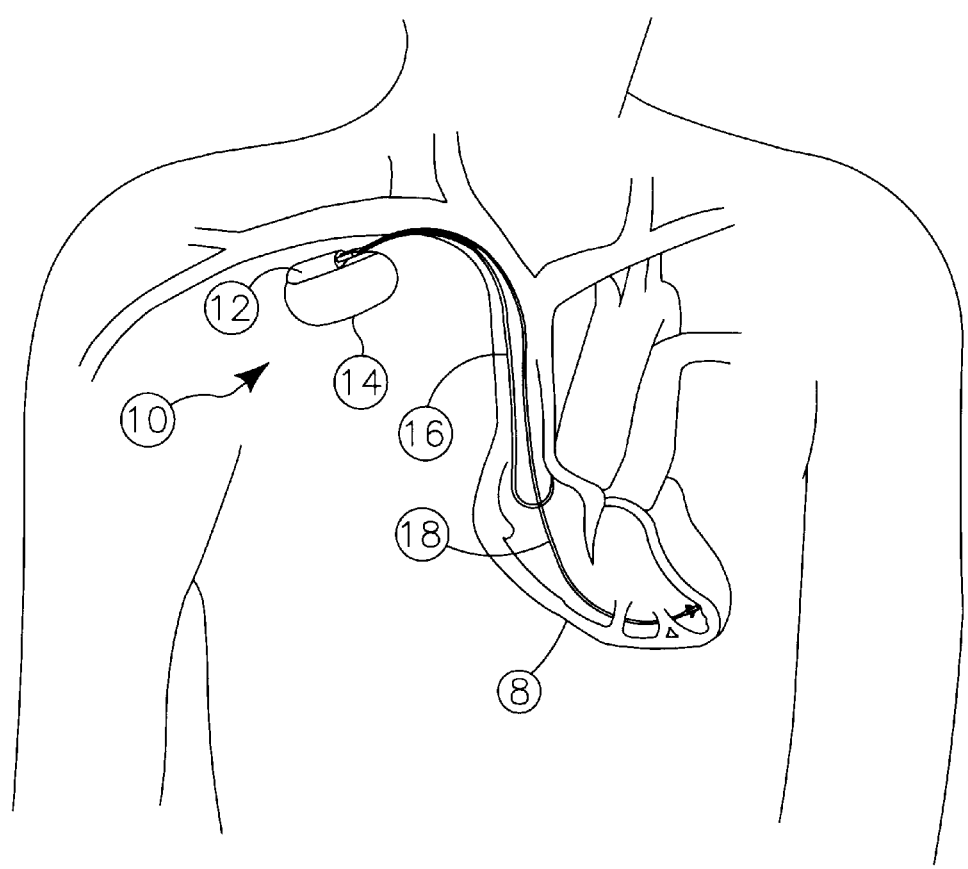
FIG. 1 is a schematic view of an implantable medical device in situ, made in accordance with one embodiment of the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18. Leads 16, 18 may be attached to hermetically sealed enclosure 14 and may be implanted near human or mammalian heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in its respective entirety.

Figure 2:
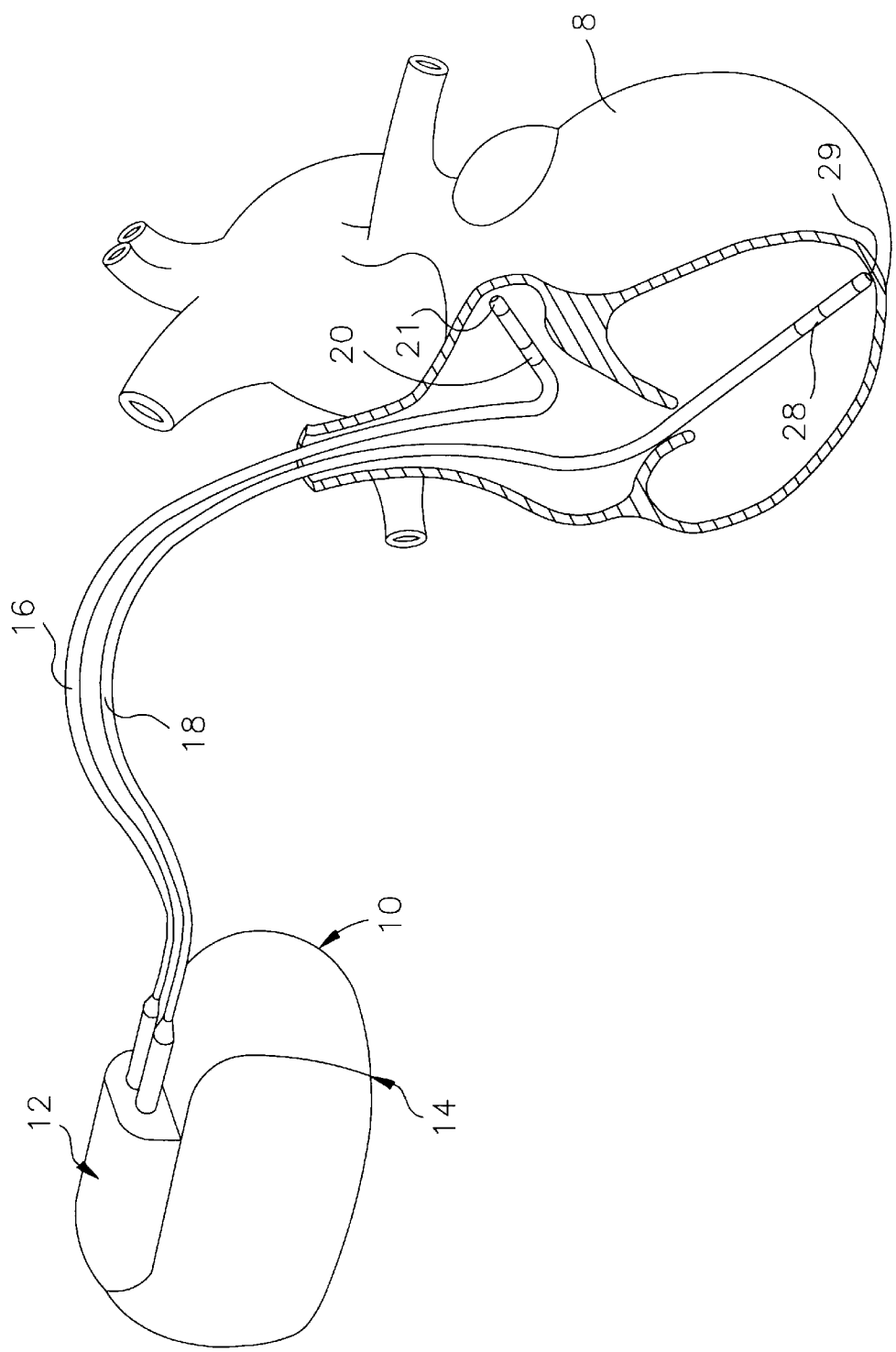
FIG. 2 is a schematic view of one embodiment of the implantable medical device of FIG. 1, made in accordance with one embodiment of the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
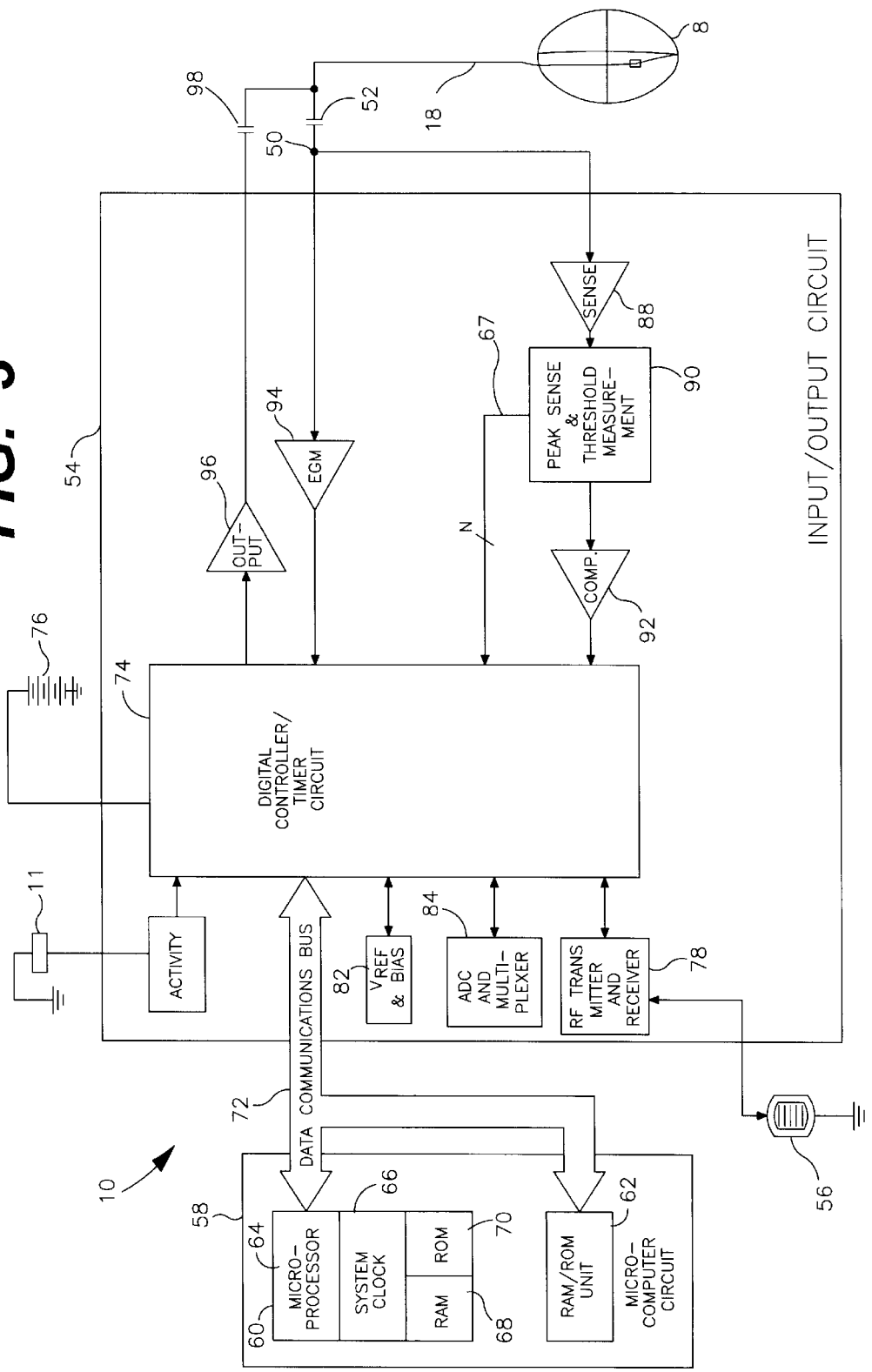
FIG. 3 is a block diagram illustrating components of an embodiment of the implantable medical device of FIG. 1, made in accordance with one embodiment of the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor 11. Activity sensor 11 may be, for example, an accelerometer based on silicon technology, a piezoceramic accelerometer or an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 may be controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 may be powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. In one embodiment of the invention, the particular programming and telemetry scheme selected permits the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI, modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
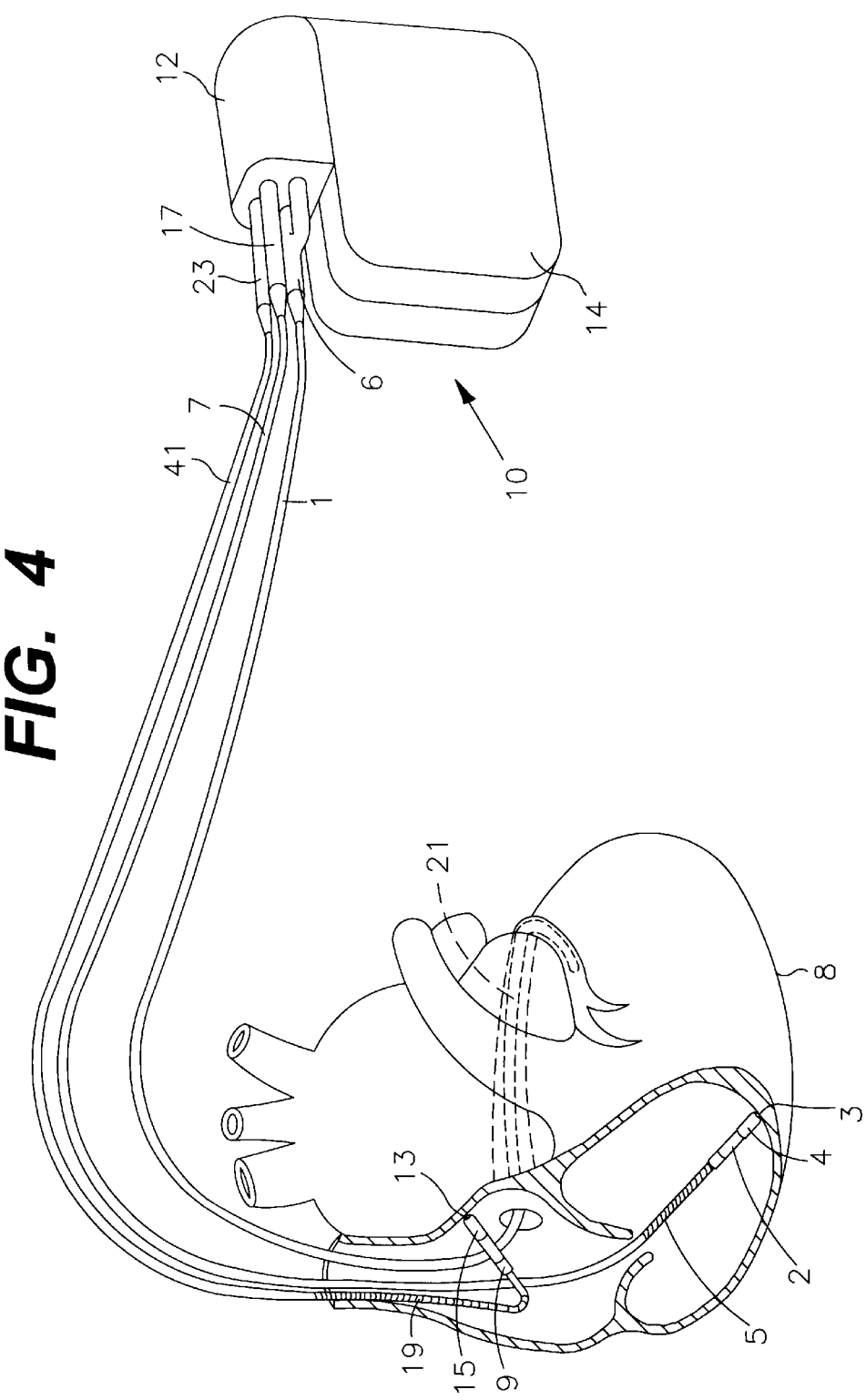
FIG. 4 is a schematic view of another embodiment of an implantable medical device, made in accordance with one embodiment of the present invention.
Figure 5:
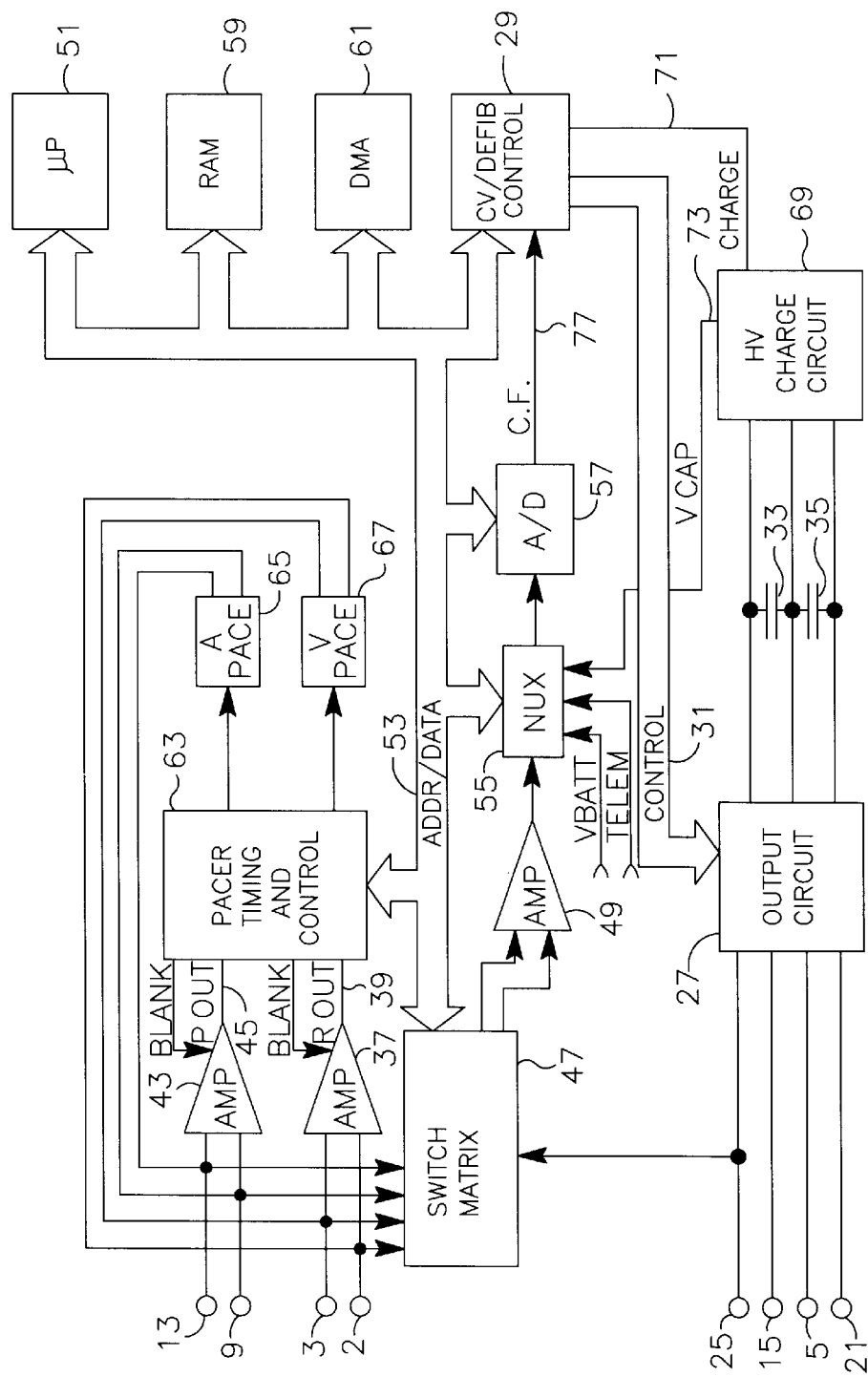
FIG. 5 is a block diagram illustrating components of an embodiment of the implantable medical device of FIG. 4, made in accordance with one embodiment of the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press*, pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in *PACE*, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachyarrhythmia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an atrial escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Figure 6:
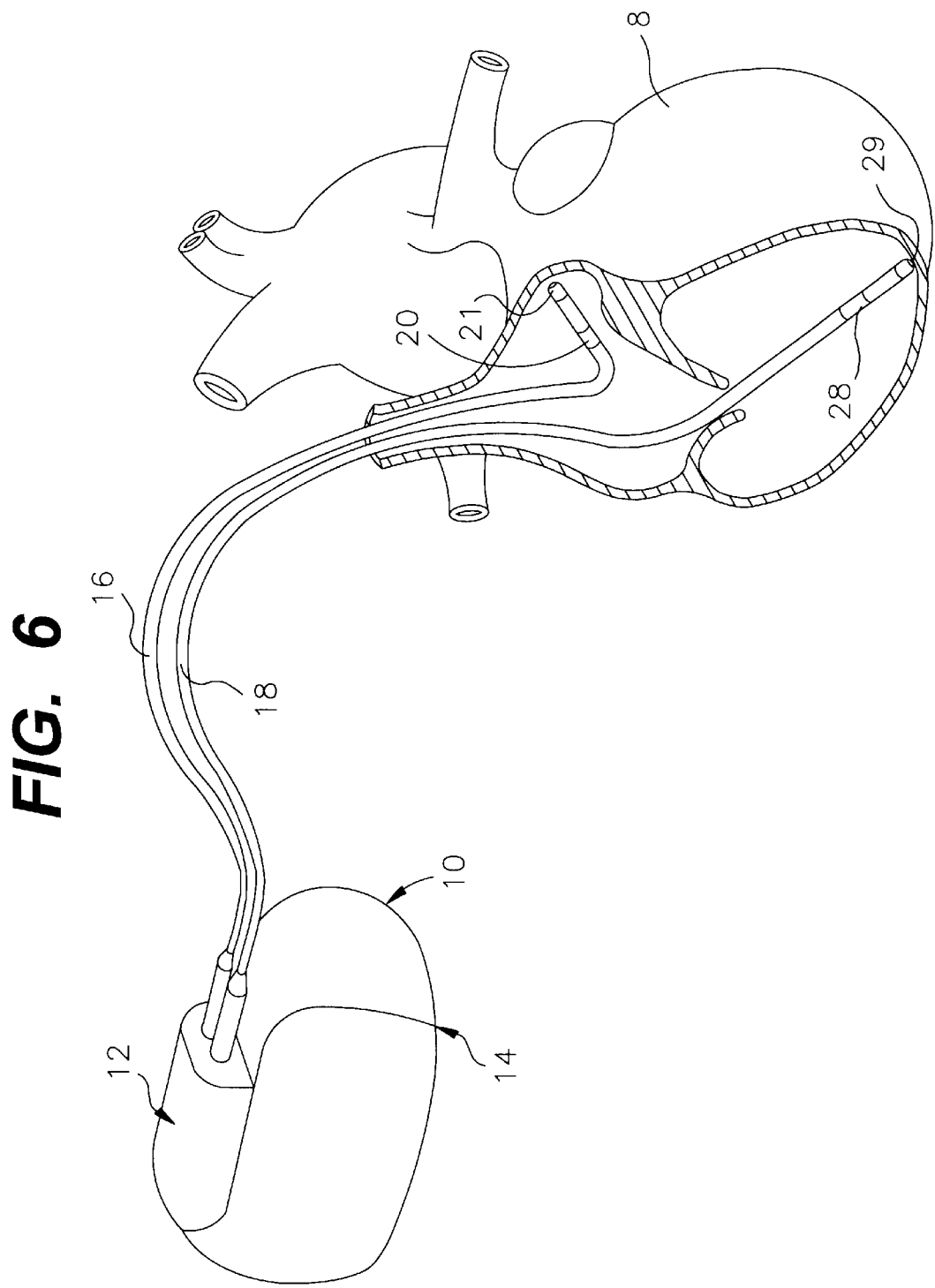
FIG. 6 is a schematic view of another embodiment of an implantable medical device, made in accordance with one embodiment of the present invention.

FIG. 6 is a simplified schematic view of one embodiment of implantable medical device ("IMD") 10 of the present invention. The IMD 10 shown in FIG. 6 is a pacemaker comprising at least one of pacing and sensing leads 16 and 18. Leads 16, 18 may be attached to hermetically sealed enclosure 14 and may be implanted near human or mammalian heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. One or more of leads 16, 18 may be used to sense polarization signals in accordance with the present invention. Leads 16, 18 may be in communication with microprocessor 51. In one embodiment of the invention, microprocessor 51 may be used to measure the magnitudes of polarizations signals sensed by one or more of leads 16, 18. Microprocessor 51 may also be able to determine a deflection differential between various magnitudes measured over time. For example, a polarization signal may be sensed during a first instance by leads 16, 18, processed by processor 51 and stored in a memory or a portion of memory of IMD 10. Such memory may be, by way of example only, RAM 68 or ROM 70 of IMD 10, where the contents of RAM 68 and ROM 70 may be accessed and consequently executed by microprocessor 51/microcomputer 58.

A subsequent polarization signal may then be sensed at a later time by leads 16, 18 and processed. This subsequent polarization signal may then be compared to the first stored polarization signal. For example, microprocessor 51 may compare the two values and, if the deflection differential of the two values is greater than an established threshold, it may be determined that the patient may be in danger of kidney failure or may already have experienced kidney failure.

The established threshold may be one or a plurality of values stored within a memory of microprocessor 51. Such memory may be, by way of example only, RAM 68 or ROM 70 of IMD 10, where the contents of RAM 68 and ROM 70 may be accessed and consequently executed by microprocessor 51/microcomputer 58. For example, in one embodiment of the invention, the established threshold may be determined with reference to a database comprising a plurality of differential values. These differential values may be determined, for example, based on the patient's history or based on clinical results. Alternatively, the differential values may be set by the physician based on the patient's history or other physician-determined factors.

In other embodiments and methods of the present invention, a series of discrete and individual historical or chronological polarization signal trends may be calculated by comparing a series of presently measured polarization signals respecting previously measured polarization signals, where the polarization trend signals are calculated and stored in memory at predetermined intervals for subsequent retrieval or signal processing. Discrete or individual polarization trend signals may also be employed to alert or warn the patient or a health care professional that the patient has a probability of or is experiencing kidney failure in response to a predetermined polarization trend signal threshold being reached or exceeded. A warning or alert may be provided to a remote health care provider through internet or telephonic communication between the implantable medical device and a remote computer, server or database. In response to a warning or alert being generated, the patient and/or health care provider being prompted to arrange dialysis treatment for the patient within a specified time period. In the above respects, the teachings of PCT Patent Application Serial No. US01/01639 entitled "System and Method of Communicating between an Implantable Medical Device and a Remote Computer System or Health Care Provider" to Haller et al. may be employed to great advantage in respect of the present invention. The entirety of the foregoing PCT patent application to Haller et al. is hereby incorporated by reference herein.

Leads 16 and 18 may have unipolar or bipolar electrodes disposed thereon, as is well known in the art. Any one or more of the electrodes disposed on leads 16, 18 may be used to sense polarization values in accordance with the present invention. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in its respective entirety.

Figure 7:
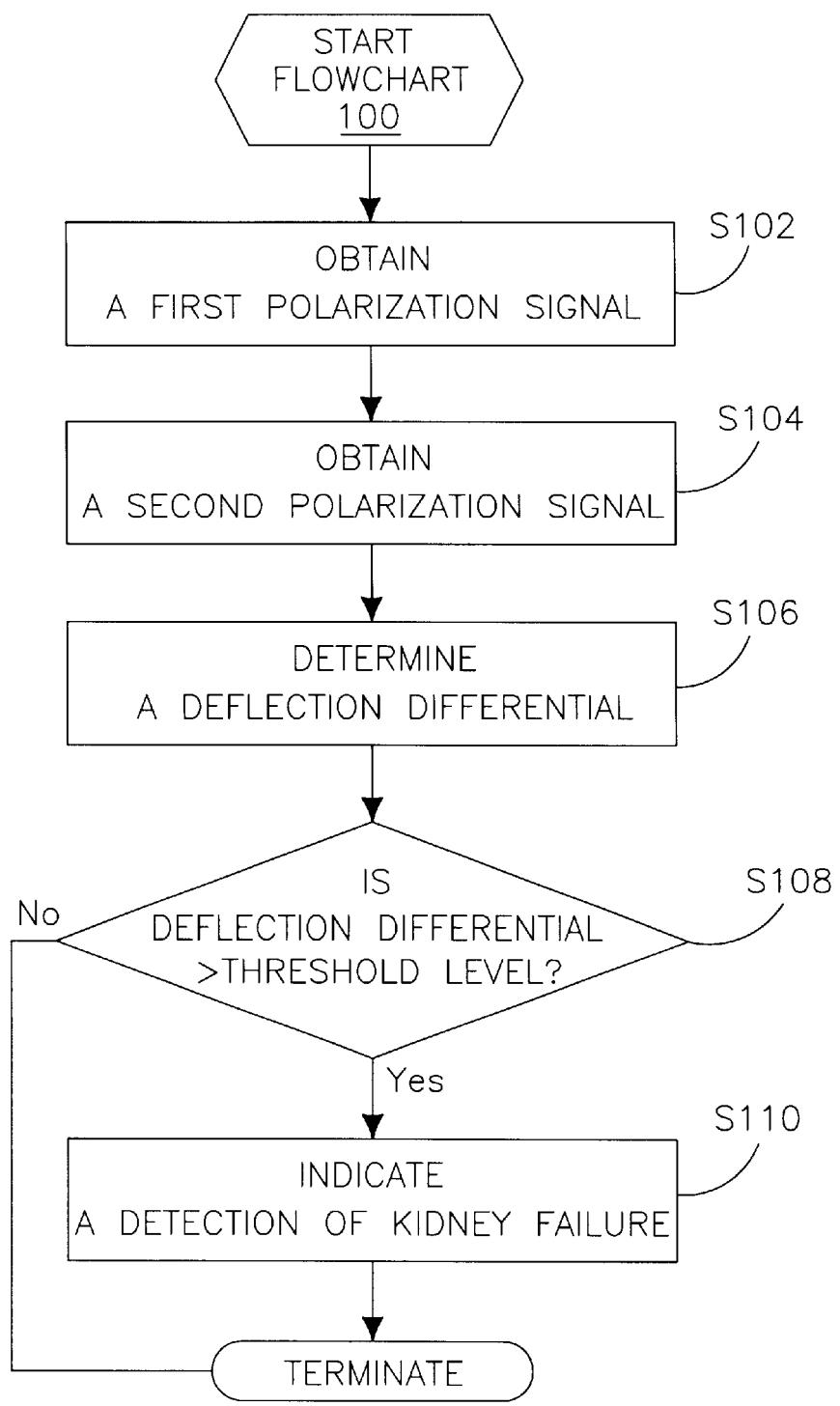
FIG. 7 is a flowchart of a kidney failure detection method as implemented by the implantable medical devices of any one or more of FIGS. 1–6 in accordance with the present invention.

FIG. 7 illustrates a flowchart 100 of a kidney failure detection method of the present invention. The description herein of flowchart 100 is based upon a utilization of IMD 10, but those having ordinary skill in the art will appreciates the applicability of flowchart 100 to various types of implantable medical devices. During a stage S102 of flowchart 100, a measurement by IMD 10 of a polarization signal is obtained during a visit by a patient carrying IMD 10 to a hospital or clinic for a first dialysis treatment. Alternatively, the polarization signal may be sensed by leads 16, 18 at any time after IMD 10 has been implanted in the patient. The magnitude of the sensed polarization signal may then be stored as described above for later comparison. Storage of the magnitude value may be performed automatically, for example by a computer algorithm and/or program capable of being stored in an electronic medium such as, by way of example only, RAM 68 or ROM 70 of IMD 10, where the contents of RAM 68 and ROM 70 may be accessed and consequently executed by microprocessor 64/microcomputer 58. Alternatively, a physician may manually cause storage of the magnitude value.

As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

Figure 8:
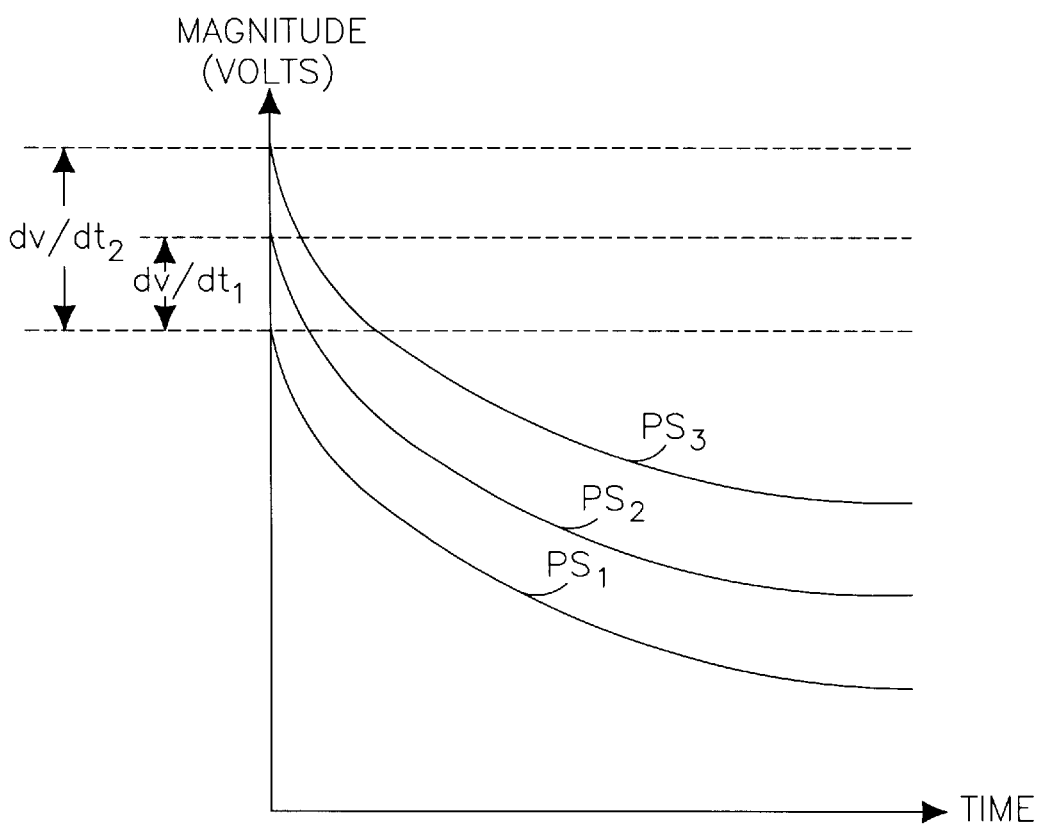
FIG. 8 is a graph of various polarization signals as measured by any one or more of the implantable medical devices of FIGS. 1–6.

FIG. 8 illustrates a polarization signal $P_{S1}$ that is representative of polarization signal obtained during stage S102. During a stage S104 of flowchart 100, a measurement by IMD 10 of a polarization signal is obtained during a subsequent visit by the patient carrying IMD 10 to a hospital or clinic for a second dialysis treatment. Alternatively, the subsequent polarization signal may be sensed by leads 16, 18 at any time after IMD 10 has been implanted in the patient. The magnitude of the subsequent sensed polarization signal may then be stored as described above for later comparison to the first sensed polarization signal. Storage of the magnitude value may be performed automatically, for example by a computer algorithm and/or program capable of being stored in an electronic medium such as, by way of example only, RAM 68 or ROM 70 of IMD 10, where the contents of RAM 68 and ROM 70 may be accessed and consequently executed by microprocessor 64/microcomputer 58. Alternatively, a physician may manually cause storage of the magnitude value.

FIG. 8 illustrates a polarization signal $P_{S2}$ and a polarization signal $P_{S3}$ whereby each signal can serve as representation of the polarization signal obtained during stage S104.

During a stage S106 of flowchart 100, a deflection differential between the measured polarization signals is determined. For example, a deflection differential $dv/dt_1$ is determined during stage S106 when polarization signal $P_{S2}$ is the measured polarization during stage S104, and a deflection differential $dv/dt_2$ is determined during stage S106 when polarization signal $P_{S3}$ is the measured polarization during stage S104. During a stage S108 of flowchart 100, it is determined in the deflection differential determined during stage S106 is greater than a threshold level.

In one embodiment of the invention, microprocessor 51 may be used to determine a deflection differential between various magnitudes measured over time. For example, microprocessor 51 may compare the magnitude value of the first sensed polarization signal to the magnitude value of the subsequent sensed polarization signal. The physician may invoke processing of the deflection differential manually or, alternatively, comparison of polarization signal magnitudes and deflection differential calculations may be automatically performed.

Flowchart 100 terminates when the deflection differential is determined to be less than a threshold level during stage S108. Otherwise, an indication of kidney failure is provided during a stage S110 of flowchart 100 when the deflection differential is determined to be greater than a threshold level during stage S108. For example, deflection differential $dv/dt_1$ can be less than the threshold level whereby no indication of kidney failure is provided, while deflection differential $dv/dt_2$ can be greater than the threshold whereby an indication of kidney failure is provided. In one embodiment of the invention, microprocessor 51 may compare the two values and, if the deflection differential of the two values is greater than an established threshold, it may be determined that the patient may be in danger of kidney failure or may already have experienced kidney failure. The established threshold may be one or a plurality of values stored within a memory of microprocessor 51. Such memory may be, by way of example only, RAM 68 or ROM 70 of IMD 10, where the contents of RAM 68 and ROM 70 may be accessed and consequently executed by microprocessor 51/microcomputer 58. For example, in one embodiment of the invention, the established threshold may be determined with reference to a database comprising a plurality of differential values. These differential values may be determined, for example, based on the patient's history or based on clinical results. Alternatively, the differential values may be set by the physician based on the patient's history or other physician-determined factors.

There are various ways in which the various stages of flowchart 100 may be implemented in IMD 10. In one embodiment, a doctor can establish a connection of IMD 10 to a computer whereby the polarization signals are graphically displayed. The doctor can thereby detect any kidney failures by a visual interpretation of the graphical display. Alternatively, IMD 10 can provide an indication of kidney failure when applicable within the graphical display. In a second embodiment, a memory of IMD 10 can store various measurements of polarization signals and provide an audible sound upon a detection of kidney failure.

In the embodiment of the invention seen in FIGS. 1 through 7, the parameters determined include: a first polarization signal magnitude, a second polarization signal magnitude, a deflection value and a potential risk of kidney failure value. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

In preferred embodiments of the present invention, the one or more electrodes employed to stimulate and produce the polarization signal on the basis of which a measure of kidney failure is derived, are special, dedicated electrodes configured for the sole purpose of measuring polarization signals or portions of such signals which lend themselves most readily to a determination of kidney failure. Accordingly, the stimulus of the present invention may be a pacing pulse (such as a pulse intended to cause contraction of heart tissue or a pulse delivered during the refractory period), or a pulse delivered in blood only so as to derive an appropriate measure of ionic concentration. The polarization signal so produced is preferably measured using DSP technology and processing techniques such as those described in U.S. Pat. No. 6,029,087 to Wohigemuth entitled "Cardiac Pacing System with Improved Physiological Event Classification Based on DSP." Employment of a DSP to sense and process polarization signals in accordance with some embodiments of the present invention provides the further advantage of permitting polarization signal voltages to be measured "directly," as opposed to measuring such signals using complicated analog circuit amplifier circuits as described hereinabove.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing determining the potential of kidney failure based on ambient heart conditions such as ionic concentration. The present invention is also not limited to the measurement of polarization signals, perse, but may find further application as a measuring means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method for determining kidney failure in a patient using an implantable medical device, the method comprising:
measuring a first magnitude of a first polarization signal;
measuring an additional magnitude of an additional polarization signal after a first interval;
determining a deflection differential between the first magnitude and the additional magnitude; and
determining whether a patient is likely to be experiencing or to experience kidney failure when the deflection differential is greater than an established threshold.

2. The method of claim 1, further comprising measuring the first magnitude of the first polarization signal during a first visit of the patient for a dialysis treatment.

3. The method of claim 2, further comprising measuring the additional magnitude of the second polarization signal during an additional visit of the patient for the dialysis treatment.

4. The method of claim 1, further comprising pacing a cardiac tissue of the patient with the implantable medical device.

5. The method of claim 4, further comprising monitoring a heart rate.

6. The method of claim 1, further comprising determining the established threshold.

7. The method of claim 1, further comprising comparing the deflection differential to a plurality of differential values to determine the established threshold.

8. The method of claim 1, further comprising setting the established threshold at a predetermined value based on a patient history.

9. The method of claim 1, further comprising storing in a memory at least one established threshold value.

10. The method of claim 1, further comprising storing the first magnitude in a memory.

11. The method of claim 1, further comprising storing the additional magnitude in a memory.

12. A method of determining kidney failure using a pacing system, the pacing system comprising at least one medical electrical lead having at least one first electrode configured for positioning in a cardiac tissue of a patient, an implantable pulse generator operably connected to the at least one medical electrical lead, and means for measuring a magnitude of a polarization signal, the method comprising:
measuring a first magnitude of a first polarization signal;
measuring an additional magnitude of an additional polarization signal after a first interval;
determining a deflection differential between the first magnitude and the additional magnitude; and
determining a kidney failure in the patient when the deflection differential is greater than an established threshold.

13. The method of claim 12, further comprising measuring the first magnitude of the first polarization signal during a first visit of the patient for a dialysis treatment.

14. The method of claim 13, further comprising measuring the additional magnitude of the second polarization signal during an additional visit of the patient for the dialysis treatment.

15. The method of claim 12, further comprising pacing the cardiac tissue of the patient with the implantable medical device.

16. The method of claim 15, further comprising monitoring a heart rate.

17. The method of claim 12, further comprising determining the established threshold.

18. The method of claim 12, further comprising comparing the deflection differential to a plurality of differential values to determine the established threshold.

19. The method of claim 12, further comprising setting the established threshold at a predetermined value based on a patient history.

20. The method of claim 12, further comprising storing at least one established threshold value in a computer memory.

21. The method of claim 12, further comprising storing the first magnitude in a computer memory.

22. The method of claim 12, further comprising storing the additional magnitude in a computer memory.

23. An implantable medical device for determining kidney failure in a patient, said device comprising:
at least one sensor lead operable to sense at least one polarization signal;
a processor operatively coupled to said at least one sensor lead;
wherein said processor is operable to measure a first magnitude of a first polarization signal during a first visit of the patient for a dialysis treatment;
wherein said processor is further operable to measure a second magnitude of a second polarization signal during a second visit of the patient for a dialysis treatment;
wherein said processor is further operable to determine a deflection differential between the first magnitude and the second magnitude; and
wherein said processor is further operable to determine a kidney failure in the patient when the deflection differential is greater than an established threshold.

24. The device of claim 23, further comprising:
at least one pacing lead operable to pace the cardiac tissue of the patient.

25. The device of claim 24 wherein the processor is further operable to monitor a heart rate of the cardiac tissue.

26. The device of claim 24 wherein the processor is further operable to determine the established threshold.

27. The device of claim 24 further comprising a database comprising a plurality of differential values, wherein the processor is further operable to determine the established threshold by comparing the deflection differential to the differential values.

28. The device of claim 23 wherein the processor is further operable to set the established threshold at a predetermined value based on a patient history.

29. The device of claim 23, further comprising a storage location for storing at least one established threshold value.

30. The device of claim 23, further comprising a storage location for storing the first magnitude.

31. The device of claim 23, further comprising a storage location for storing the second magnitude.

32. An implantable medical device, comprising:
an implantable pulse generator;
at least one medical electrical lead operably connected to the implantable pulse generator, the medical electrical lead having at least one first electrode configured for positioning in a cardiac tissue of a patient; and
a processor operably adapted to measure a first magnitude of a first polarization signal in the cardiac tissue of the patient and to measure an additional magnitude of an additional polarization signal after a first interval;
the processor further operably adapted to determine a deflection differential between the first magnitude and the additional magnitude; and
to determine a kidney failure in the patient when the deflection differential is greater than an established threshold.

33. The device of claim 32, further comprising at least one pacing lead operably adapted to pace the cardiac tissue of the patient.

34. The device of claim 32, wherein the processor is further operably adapted to monitor a heart rate of the cardiac tissue.

35. The device of claim 32, wherein the processor is further operably adapted to determine the established threshold.

36. The device of claim 32, further comprising a database comprising a plurality of differential values, wherein the processor is further operably adapted to determine the established threshold by comparing the deflection differential to the differential values.

37. The device of claim 32, wherein the processor is further operably adapted to set the established threshold at a predetermined value based on a patient history.

38. The device of claim 32, further comprising a memory location operably connected to the processor for storing at least one established threshold value.

39. The device of claim 32, further comprising a memory location operably connected to the processor for storing the first magnitude.

40. The device of claim 32, further comprising a memory location operably connected to the processor for storing the second magnitude.

41. An implantable medical system for determining kidney failure in a patient, the system comprising:
at least one medical electrical lead having at least one first electrode configured for positioning in a cardiac tissue of the patient;
an implantable pulse generator operably connected to the at least one medical electrical lead;
means for measuring a first magnitude of a first polarization signal;
means for measuring an additional magnitude of an additional polarization signal after a first interval;
means for determining a deflection differential between the first magnitude and the additional magnitude; and
means for determining a kidney failure in the patient when the deflection differential is greater than an established threshold.

42. The system of claim 41, further comprising means for measuring the first magnitude of the first polarization signal during a first visit of the patient for a dialysis treatment.

43. The system of claim 41, further comprising means for measuring the additional magnitude of the second polarization signal during an additional visit of the patient for the dialysis treatment.

44. The system of claim 41, further comprising means for pacing the cardiac tissue of the patient.

45. The system of claim 41, further comprising means for monitoring a heart rate of the cardiac tissue.

46. The system of claim 41, further comprising means for determining the established threshold.

47. The system of claim 41, further comprising means for comparing the deflection differential to a plurality of differential values to determine the established threshold.

48. The system of claim 41, further comprising means for setting the established threshold at a predetermined value based on a patient history.

49. The system of claim 41, further comprising means for storing at least one established threshold value.

50. The system of claim 41, further comprising means for storing the first magnitude.

51. The system of claim 41, further comprising means for storing the additional magnitude.

52. System means for implementing a computer useable medium including a computer program for determining kidney failure in a patient using a pacing system, the pacing system comprising at least one medical electrical lead having at least one first electrode configured for positioning in a cardiac tissue of a patient, an implantable pulse generator operably connected to the at least one medical electrical lead, and means for measuring a magnitude of a polarization signal, the system implementing means comprising:
means for implementing computer program code that measures a first magnitude of a first polarization signal;
means for implementing computer program code that measures an additional magnitude of an additional polarization signal after a first interval;
means for implementing computer program code that determines a deflection differential between the first magnitude and the additional magnitude; and
means for implementing computer program code that determines a kidney failure in the patient when the deflection differential is greater than an established threshold.

53. The program of claim 52, further comprising means for implementing computer program code that measures the first magnitude of the first polarization signal during a first visit of the patient for a dialysis treatment.

54. The program of claim 52, further comprising means for implementing computer program code that measures the additional magnitude of the second polarization signal during an additional visit of the patient for the dialysis treatment.

55. The program of claim 52, further comprising means for implementing computer program code that paces the cardiac tissue of the patient.

56. The program of claim 52, further comprising means for implementing computer program code that monitors a heart rate of the cardiac tissue.

57. The program of claim 52, further comprising means for implementing computer program code that determines the established threshold.

58. The program of claim 52, further comprising means for implementing computer program code that compares the deflection differential to a plurality of differential values to determine the established threshold.

59. The program of claim 52, further comprising means for implementing computer program code that sets the established threshold at a predetermined value based on a patient history.

60. The program of claim 52, further comprising means for implementing computer program code that stores at least one established threshold value.

61. The program of claim 52, further comprising means for implementing computer program code that stores the first magnitude.

62. The program of claim 52, further comprising means for implementing computer program code that stores the additional magnitude.

* * * * *